United States Patent
Fietzek

(10) Patent No.: US 10,837,948 B2
(45) Date of Patent: Nov. 17, 2020

(54) DEVICE FOR DETECTION OF A PARTIAL PRESSURE AND METHOD FOR ITS OPERATION

(71) Applicant: Kongsberg Maritime Contros GmbH, Kiel (DE)

(72) Inventor: Peer Fietzek, Kiel (DE)

(73) Assignee: Kongsberg Maritime Contros GmbH, Kiel (DE)

(*) Notice: Subject to any disclaimer, the term of this patent is extended or adjusted under 35 U.S.C. 154(b) by 210 days.

(21) Appl. No.: 16/003,832

(22) Filed: Jun. 8, 2018

(65) Prior Publication Data
US 2018/0292371 A1  Oct. 11, 2018

Related U.S. Application Data

(62) Division of application No. 13/767,606, filed on Feb. 14, 2013, now Pat. No. 10,018,606.

(30) Foreign Application Priority Data

Feb. 17, 2012 (DE) .......... 10 2012 101 313

(51) Int. Cl.
G01N 33/00 (2006.01)
G01N 21/3504 (2014.01)

(52) U.S. Cl.
CPC ..... *G01N 33/0004* (2013.01); *G01N 21/3504* (2013.01); *Y10T 436/214* (2015.01)

(58) Field of Classification Search
CPC .................................................. G01N 33/0004
See application file for complete search history.

(56) References Cited

U.S. PATENT DOCUMENTS 3,929,588 A    12/1975  Parker et al.
3,951,603 A  *  4/1976  Obayashi .............. G01N 27/12
                                                         436/131
(Continued)

FOREIGN PATENT DOCUMENTS

DE     2929387 A1    1/1981
DE     3782921 T2    4/1993
(Continued)

OTHER PUBLICATIONS

Search report, and English translation thereof, dated Jan. 10, 2013, in German Patent Application No. 102012101313.6 (13pgs).

*Primary Examiner* — Harshad R Patel
*Assistant Examiner* — Alex T Devito
(74) *Attorney, Agent, or Firm* — North Weber and Baugh LLP; Michael North

(57) ABSTRACT

In order to provide a device for detection of a partial pressure of a measurement gas contained in a surrounding gas, comprising a measurement space with at least one inlet opening to admit surrounding gas into the measurement space and at least one outlet opening to discharge surrounding gas from the measurement space, a quantity that characterizes the partial pressure of the measurement gas in the measurement gas sensor sensitive to the measurement gas to measure a quantity that characterizes the partial pressure of the measurement gas in the measurement space, as well as readout device to read out the measurement gas sensor as well as a method for its operation, which permit metrological detection of the partial pressure of a measurement gas contained in a surrounding gas with improved chronological and spatial resolution, it is proposed that means to determine a response characteristic of device be provided.

9 Claims, 4 Drawing Sheets

(56) References Cited

U.S. PATENT DOCUMENTS

| | | | |
|---|---|---|---|
| 4,039,933 A * | 8/1977 | Moran | G01D 18/004 |
| | | | 324/425 |
| 4,056,098 A | 11/1977 | Michel et al. | |
| 4,171,915 A * | 10/1979 | Hesselink | G01N 21/45 |
| | | | 356/517 |
| 4,173,975 A | 11/1979 | DeLong et al. | |
| 4,543,176 A | 9/1985 | Harada et al. | |
| 4,940,528 A | 7/1990 | Oki et al. | |
| 5,792,938 A | 8/1998 | Gokhfeld | |
| 2006/0201503 A1 | 9/2006 | Breen | |

FOREIGN PATENT DOCUMENTS

| | | |
|---|---|---|
| DE | 19605246 A1 | 8/1997 |
| DE | 3752118 T2 | 2/1998 |
| DE | 69712053 T2 | 11/2002 |
| DE | 69731445 T2 | 11/2005 |
| DE | 102006006540 A1 | 8/2007 |
| DE | 102007029154 A1 | 1/2008 |
| DE | 102007054391 A1 | 5/2009 |
| DE | 112008001147 T5 | 4/2010 |
| DE | 102010039392 A1 | 2/2012 |

\* cited by examiner

DEVICE FOR DETECTION OF A PARTIAL PRESSURE AND METHOD FOR ITS OPERATION

CROSS REFERENCE TO RELATED APPLICATIONS

This application is a divisional of previously filed copending U.S. patent application Ser. No. 13/767,606, filed Feb. 14, 2013, which application claims priority to German Patent Application No. 102012101313.6, filed Feb. 17, 2012, which applications are hereby incorporated herein by reference in their entireties.

BACKGROUND

A. Technical Field

The present invention concerns a device for detection of a partial pressure of a measurement gas contained in a surrounding gas, comprising a measurement space with at least one inlet opening to admit surrounding gas to the measurement space and at least one outlet opening to discharge the surrounding gas from the measurement space, a measurement gas sensor sensitive to the measurement gas to measure a quantity that characterizes the partial pressure of the measurement gas in the measurement space, as well as a readout device to read out the measurement gas sensor. The surrounding gas in the context of the invention can also be dissolved in a liquid, especially water, oil or another liquid occurring in the oil and gas industry. In the individual case the inlet opening can be identical to the outlet opening in the context of the invention.

The present invention also concerns a method for operation of a measurement gas sensor in a measurement space and sensitive to the measurement gas for measurement of a quantity that characterizes the partial pressure of the measurement gas in the measurement space, comprising a device, especially according to one of the claims 1 to 9, for detection of a partial pressure of a measurement gas contained in a surrounding gas.

B. Background of the Invention

A device of the type just mentioned as well a method for its operation are known, for example, from DE102006035788. Such devices are used, for example, for metrological detection of gases. With an appropriate configuration, especially where a membrane separates the measurement space from the surrounding gas, gas measurements under water in particular can be conducted with such devices. Leakage detection on underwater pipelines or other underwater structures as well as localization in general of artificial and natural gas leaks on the sea bottom for technical or scientific purposes are among the application areas of the generic detection device.

In many cases it is essential in such applications to conduct measurements under conditions in which the partial pressure in the measurement gas contained in the surrounding gas, which is to be detected by the known device, is variable over time. This can be due to the fact that a time change in partial pressure of the measurement gas occurs when the detection device is arranged stationary. On the other hand, this can be the cases, if an essentially stationary partial pressure of the measurement is detected by moving the detection device according to the invention through a measurement area with spatially different partial pressures of the measurement gas. In such cases it is important for optimal detection of the partial pressure of the measurement gas contained in the surrounding gas that spatial and chronological assignment of the measurement signals of the measurement gas sensor to the actual conditions of the surrounding gas is possible. However, it has been shown that adequate chronological or spatial assignment is not possible in many cases in the known device.

The task of the present invention is therefore to provide a device and a method of the type just mentioned which make possible metrological detection of the partial pressure of a measurement gas contained in a surrounding gas with improved chronological and spatial resolution.

This task is solved according to the invention with a generic device in which means to determine a response characteristic of the device are provided.

SUMMARY OF THE INVENTION

In an embodiment of the invention the means to determine a response characteristic can include a correction gas sensor sensitive to a correction gas to measure a measurement quantity that characterizes a partial pressure of the correction gas in the measurement space, as well as readout devices to read out the correction gas sensor, in which case the correction gas is different from the measurement gas contained in the surrounding gas. Through this expedient a zeroing can be conducted without measurement gas having a partial pressure above a detection threshold being present in the surrounding gas.

In particular, according to the invention the means to determine the response characteristic include means for flow of reference gas through the measurement space, to which the measurement gas sensor and/or the correction gas sensor is not sensitive. This expedient advantageously makes it possible to conduct so-called zeroing of the measurement gas sensor, as required, in situ. In the zeroing methods that are known per se conditions are created in the detector that lead to reference point measurement of the detector by supplying a gas or gas mixture to the detector to which it does not respond. Starting from this defined reference state, the response behavior of the measurement device can be metrologically detected and characterized by an appropriate method. This again permits computer compensation of the response behavior from the measurement data obtained in normal measurement operation. Relative to an ordinary zeroing of the device ex situ, for example, in a laboratory, a variety of advantages are obtained. In particular, during in situ zeroing it is ensured that any dependence of the response behavior on the surrounding parameters, for example, temperature and pressure, is taken into account. This form of zeroing is especially suited for cases in which sufficient measurement gas is contained in the surrounding gas during zeroing.

According to a preferred variant of the device according to the invention it has a reference gas source to provide reference gas. The reference gas source in the simplest case can be a cartridge or similar device, which is filled with the reference gas. The means to traverse the measurement space with the reference gas according to this variant would cause flow through the measurement space with the contents of this cartridge, on the one hand, and blocking of the measurement space relative to the surrounding gas, on the other.

According to a particularly favorable embodiment the reference gas source is designed to generate reference gas from the surrounding gas. The need to provide a supply of reference gas advantageously drops out according to this variant.

In particular, the reference gas source can include means to remove measurement gas from the surrounding gas in order to generate the reference gas from the surrounding gas. For example, the surrounding gas can be retained in the reference gas source by chemically bonding it there. For example, in the case of a measurement gas sensor sensitive to $CO_2$ the reference gas source can include a column of a chemical that absorbs $CO_2$, like soda lime or ascarite. Removal of the $CO_2$ from the surrounding gas occurs in this case in known fashion by converting the $CO_2$ to $C_aCO_3$. Activated carbon can also be used to bond hydrocarbons in order to generate a reference gas from the surrounding gas when the measurement gas sensor is sensitive to hydrocarbons. The reference gas source according to the invention can likewise include means for chemical conversion of the measurement gas so that the measurement gas sensor and/or the correction gas sensor are not sensitive to gaseous conversion products that form during the conversion. For example, oxidation of the measurement gas can be conducted, preferably using the oxygen fraction present in the surrounding gas. Oxygen from a reservoir or an oxygen source can also be used in the context of the invention. In particular, in the case of a measurement gas sensor sensitive to $CH_4$ the methane can be oxidized to carbon dioxide by means of a catalytic oxidation sensor or thermocatalytic element. In the case of a measurement gas sensor sensitive to water vapor the chemical conversion can be conducted by means of magnesium perchlorate (hydrate), $Mg(ClO_4)_2$, by means of calcium sulfate ($C_aSO_4$) or by means of silica gel ($SiO_2$).

Since the surrounding gas, especially during performance of the measurement under water, always has a moisture fraction in practice, i.e., a water fraction, zeroing can also be produced by temporarily removing the water fraction from the surrounding gas. The correction gas sensor is then used as a sensor that is sensitive to the water fraction contained in the surrounding gas so that the gaseous water fraction contained in the surrounding gas functions as correction gas. Dry surrounding gas is a reference gas for this correction gas sensor. In this case any appropriate means can be used as reference gas source in order to dry the surrounding gas to remove the water fraction from it. Silica gel is suitable for this purpose.

In a modification of the detection device according to the invention a control and evaluation unit can be provided to control the means for passage through the measurement space in order to initiate and stop flow of reference gas through the measurement space. By means of the control and evaluation unit zeroing with a reference gas can therefore be advantageously conducted in situ. In particular, on suspicion of altered surrounding conditions, zeroing can be repeated in situ in order to record a changed response characteristic.

It is particularly favorable in an embodiment of the invention, if the control and evaluation unit is designed for computer determination of a response behavior from a time series of measurement data recorded via the readout device. This permits according to the invention activation by means of the control and evaluation unit of the means for flow of reference gas through the measurement space in order to generate a reference state. By means of the control and evaluation unit a sequence of measurement data can then be recorded as soon as the means for flow of reference gas through the measurement space is deactivated again and surrounding gas again enters the detection device according to the invention. The response characteristic can be determined based on an appropriate mathematical model or otherwise. Advantageously, the dynamic response behavior determined in this way includes all effects that delay response of the measurement gas sensor. These include, in addition to the dynamics of the measurement gas sensor itself, also the delays that the surrounding gas encounters on entering the measurement space. This is of particular significance during use of the membrane, via which the surrounding gas enters the measurement space.

A particularly favorable embodiment of the invention proposes that the control and evaluation unit be configured for computer compensation of a response behavior of the measurement data recorded via the readout device. In this way it is possible to determine a chronologically or spatially correct assignment of measurement data to the actual spatial or chronological changes in partial pressure of the measurement gas. On the one hand, a response characteristic previously entered in the evaluation and evaluation unit [sic] can be used for computer compensation of the chronological response behavior. On the other hand, a chronological response behavior determined in situ can be used for computer compensation.

In particular, the control and evaluation unit can be designed to execute a method according to one of the claims.

In order to be able to use the device according to the invention under water, in a special embodiment of the invention a membrane permeable to the surrounding gas is arranged upstream of the inlet opening and/or downstream of the outlet opening so that the surrounding gas reaches the measurement space through the membrane and/or the surrounding gas leaves the device through the membrane.

Especially when a membrane is arranged in the gas inlet, it is advantageous according to the invention to be able to perform the dynamic response behavior in situ for the given surrounding parameters. The temperature response behavior in the case is also influenced by the properties of the membrane.

In order to be able to properly conduct in situ zeroing a bypass line that connects the inlet opening to the outlet opening can be provided. Especially in cases in which the reference gas is generated from the surrounding gas, the surrounding gas situated in the measurement space can be passed through the reference gas source in order to generate the reference gas from the surrounding gas instead of being released back to the surroundings by means of the bypass line.

In particular, the measurement gas sensor and/or the correction gas sensor according to the invention can include an optical measurement gas sensor, preferably a nondispersive infrared sensor and/or a spectrometer based on a tunable laser diode and/or the sensor based on a tunable laser diode, and/or a pump can be provided in order to circulate the surrounding gas through the measurement space. An optical measurement gas sensor in cooperation with a pressure and/or temperature measurement of the surrounding gas entering the measurement space is suitable for determining the partial pressure of the measurement gas.

In the case of a device for use in liquids, where the surrounding gas is dissolved in the liquid and enters the measurement space through a membrane, a pump can be provided in order to uniformly expose the membrane from the outside with liquid containing dissolved surrounding gas and thus accelerate the equilibration process.

With respect to the method the task underlying the invention is solved with a method of the type mentioned in the introduction, which includes a method for determination of a response characteristic of the measurement gas sensor, in which (a) the measurement space is traversed with a reference gas, to which the measurement gas sensor and/or correction gas sensor sensitive to a correction gas is not sensitive, in which case an output signal of the measurement gas sensor and/or an output signal of the correction gas sensor is simultaneously observed until an essentially constant minimal value is reached; (b) the measurement space is traversed with a surrounding gas after the initial signal has reached an essentially constant minimal value; during which, with the beginning of flow of surrounding gas, the output signal of the measurement gas sensor and/or the output signal of the correction gas sensor is recorded in a measurement series in time-resolved fashion during a calibration interval; (c) the response characteristic is determined by means of evaluation of the measurement series, in which at least steps (a) and (b) are conducted in situ.

In order to be able to conduct zeroing, if no reference measurement gas or a percentage of measurement gas too small for detection is contained in the surrounding gas, in a modification of the invention a correction response characteristic based on the output signal of the correction gas sensor can initially be determined for evaluation of the measurement series and then the response characteristic of the device determined from the correction response characteristic. For determination of the response characteristic of the device, starting from the correction response characteristic, results obtained by laboratory experiments can be resorted to according to the invention.

The method according to the invention advantageously permits determination of a response behavior of the device in situ, i.e., directly in the surroundings in which the device for detection of a partial pressure of a measurement gas contained in the surrounding gas is used. Since the response characteristic might [be influenced] by surrounding parameters, like temperature or pressure, it is advantageously possible by means of the method according to the invention to determine the response characteristic of the entire measurement system of the device with consideration of the corresponding surrounding conditions. This again advantageously permits a better chronological or spatial assignment of measured values to the actual measured quantity to be obtained. Owing to the fact that determination of the response characteristic occurs in situ, on the one hand, and that the response characteristic of the entire measurement device and not merely the isolated measurement gas sensor occurs, on the other hand, it is also ensured that all quantities that influence the response characteristic, like properties of a membrane contained in the inlet and outlet flow path, are considered. The method according to the invention therefore advantageously permits detection of changes of the membrane that influence the measurement, like changes in membrane thickness, conditioning, flow, or the condition with respect to overgrowth or clogging. The method according to the invention also permits reference point calibration of the measurement gas sensor when an essentially constant minimal value is reached, since it is known that no measurement gas is detected at this value.

In an embodiment of the method according to the invention, it is proposed that the output signal of the measurement gas sensor be corrected by means of the response characteristic in order to obtain a chronological assignment of the output signal for the partial pressure of the measurement gas at the time of recording of the output signal. In this way the method according to the invention permits detection of the partial pressure of a measurement gas contained in the surrounding gas corrected by the response characteristic. This is particularly advantageous, if spatial or chronological changes of the partial pressure of the measurement gas are expected, for example, because the detection device is moved through a measurement area.

If in another advantageous embodiment of the method according to the invention the calibration time interval is chosen so that the partial pressure of the measurement gas and/or that of the correction gas are essentially constant during the calibration time interval, a particularly precise determination of the response characteristic is possible. In the method for determining the response characteristic defined input and output states are present, which are not variable so that the response characteristic can be determined as a transient response during the calibration time interval.

The method according to the invention is further improved, if a first section of the measurement series which was recorded during a mixing phase of the surrounding gas with the reference gas in the measurement space is not considered for determination of the response characteristic. It has been shown experimentally that the response characteristic that is measurable within the calibration interval can be described in a first section of the measurement series with a different mathematical model than the response characteristic in a second section of the measurement series connected to the first section. The inventors suspect that the behavior in the first section of the measurement series is attributed to the fact that the reference gas must initially be replaced by the surrounding gas in the measurement space. Since this mixing phase is related to the zeroing method and drops out in normal measurement operation, it was empirically shown that for correction of measured values in normal measurement operation a response characteristic in which the said first section of measurement series is left out of consideration is best suited relative to the previously determined response characteristic.

In particular, in a preferred embodiment of the method according to the invention the first section of the measurement series can extend to a transition point from an essentially linear to an essentially exponential trend. Determination of this transition point can occur according to the invention by initially conducting a linear regression of the initial values of the measurement series and in the second step determining the residuum between the measured values and the regression lines. As soon as this residuum surpasses a predetermined threshold value, the transition point is reached. To determine the transition point an evaluation of the chronological rate of change of the measured values can likewise be conducted according to the invention, in which the transition point is characterized by a significant reduction of the rate of change.

In a preferred embodiment of the method according to the invention the response characteristic is determined by means of regression analysis of the measurement series, in which case the following model is preferably applied:

$$p_{(t)} = p_{water} + (p_{(t_0)} - p_{water})e^{-\frac{t}{\tau}}$$

in which $p_{(t)}$ denotes the output signal at time t, $p_{water}$ denotes the partial pressure of the measurement gas within the surrounding gas, $p_{(t_o)}$ denotes the output signal at time $t_0$ and $\tau$ denotes a time constant. It has been shown that a correction of the measured values by means of the response characteristic determined with the known formula, characterized by parameter τ, is particularly suitable for detecting the real value of the measured quantity.

In a preferred embodiment of the method according to the invention the output signal of the measurement gas sensor is corrected by means of the response characteristic by assigning the output signal $p_{(t)}$ at time τ to the partial pressure $p_{water}$ of the measurement gas within the surrounding gas at the time of recording of the output signal according to the following formula:

$$p_{water} = \frac{p_{(t)} - p_{(t_0)}e^{-\frac{t}{\tau}}}{1 - e^{-\frac{t}{\tau}}}$$

in which $p_{(t_o)}$ denotes the output signal at time $t_o$.

An iterative correction of the output signal of the measurement gas sensor by means of the response characteristic can be obtained in this sense especially with the following formula:

$$p_{corrected, t_{i+1}} = \frac{p_{(t+1)} - p_{(t_i)}e^{-\frac{\Delta t}{\tau}}}{1 - e^{-\frac{\Delta t}{\tau}}} \text{ with } \Delta t = t_{i+1} - t_i$$

The interval ΔT, i.e., the scanning rate, must be chosen at least small enough so that the partial pressure of the measurement gas can be assumed constant with an interval ΔT. This is guided according to the partial pressure gradient of the measurement gas, which is to be expected during the corresponding measurement. On the other hand, the scanning rate is also guided according to the rate at which the detection device is moved through the measurement medium.

In a modification of the method according to the invention it is proposed that the method for determination of a response characteristic be conducted several times, especially after any significant change of one or more surrounding parameters. For example, if a temperature change or pressure change is established, according to this embodiment of the invention a repeated determination of the response characteristic is conducted.

The invention is described as an example in a preferred variant with reference to a drawing in which additional advantageous details can be deduced from the figures of the drawing.

Functionally identical parts are then provided with the same reference numbers.

DETAILED DESCRIPTION OF THE PREFERRED EMBODIMENTS

Figure 1:
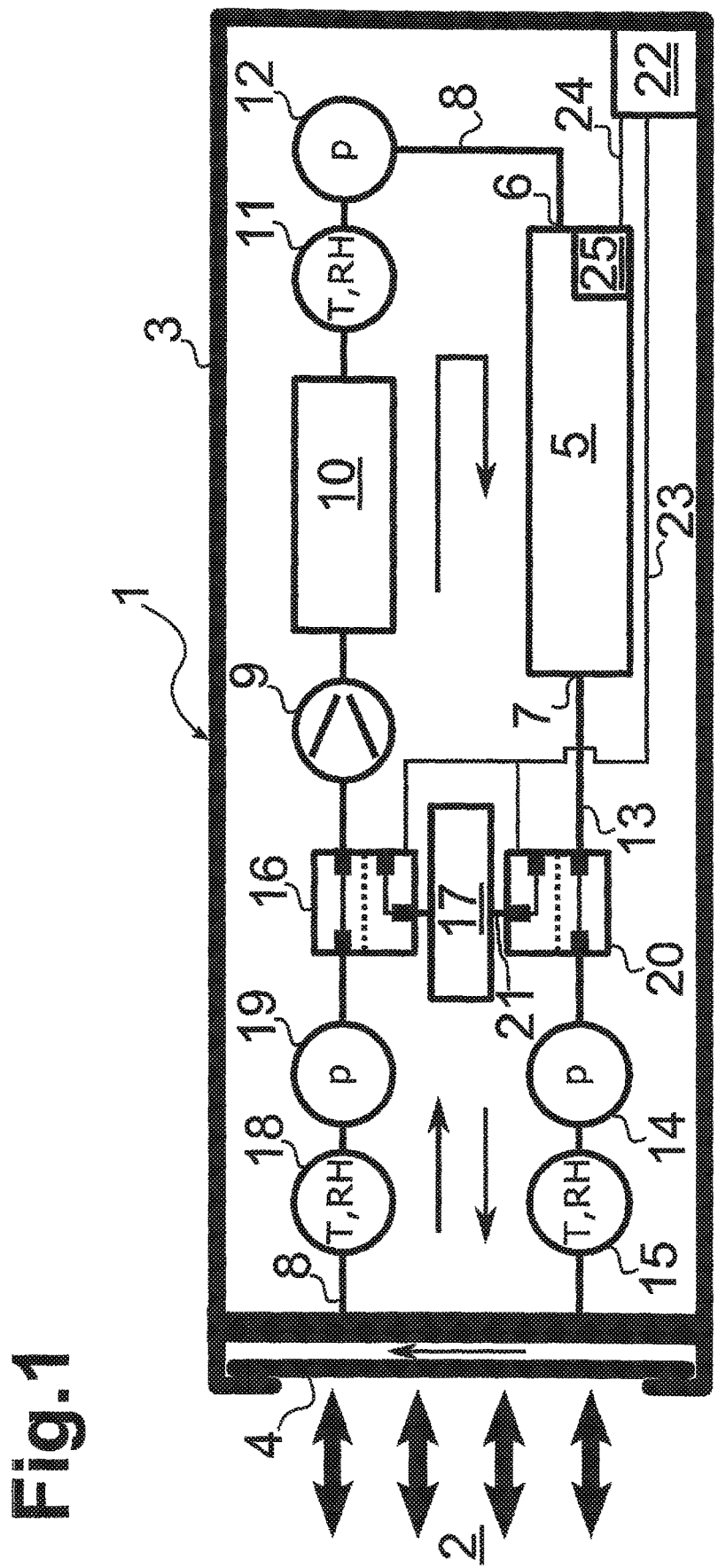
FIG. 1: schematic depiction of a preferred variant for underwater use of a detection device according to the invention.

FIG. 1 shows in a schematic sectional view a partial pressure sensor 1, which is immersed in water 2. The partial pressure sensor 1 has a watertight housing 3. The watertight housing 3 is open on one side to the surrounding water 2 via a membrane equilibrator 4. The membrane equilibrator 4 is permeable to the surrounding gas contained in the surrounding water 2 but not to water. A measurement gas sensor 5 is arranged as core piece in the interior of the partial pressure sensor 1 delimited by housing 3 and the membrane equilibrator 4 from the surrounding water 2. This is formed as a non-dispersive infrared detector in the practical example depicted here. The measurement gas sensor 5 has an inlet opening 6 and an outlet opening 7. A measurement space not explicitly shown is arranged within the measurement gas sensor 5 in the schematic depiction according to FIG. 1.

In addition, an inlet line 8 for the surrounding gas connected to the surroundings via the membrane equilibrator 4 permeable to the surrounding gas contained in water 2 and in turn containing carbon dioxide as measurement gas is arranged in interior housing 3.

The inlet line 8 discharges in inlet opening 6 of the measurement gas sensor 5. A pump 9 and a heating device 10 downstream of pump 9 to heat the surrounding gas that enters inlet line 8 are arranged in the inlet line 8. Downstream of the heating device 10 a sensor 11 for temperature and moisture as well as a pressure sensor 12 are arranged in succession in the inlet line 8. The outlet line 7 of the measurement gas sensor 5 discharges in an outlet line 13, which communicates with the surrounding water 2 via the membrane equilibrator 4. A pressure sensor 14 and a temperature and moisture sensor 15 are also arranged in the outlet line 13.

Upstream of pump 9 a valve 16 is arranged in inlet line 8. The values 16 is configured is that it produces in the first switching state a connection of the suction side of pump 9 with a section of inlet line 8 facing the membrane equilibrator 4. This switching state is sketched in FIG. 1. In the second possible switching state of the valve, which valve 16 can assume, the suction side of pump 9 of inlet line 8 is connected to a reference gas source 17 so that the section of the inlet line 8 between membrane equilibrator 4 and valve 16 does not communicate with the suction side of pump 9. In this section of the inlet line 8 a sensor 18 for temperature and moisture as well as a pressure sensor 19 are also provided.

A valve 20 is arranged in the outlet line 13 upstream of sensor 15 for temperature and moisture as well as pressure sensor 14. Valve 20 in the outlet line 13 is designed similar to the valve 16 and inlet line 8 and can also assume two possible switching states. The first possible switching state of valve 20 and outlet line 13 is the one depicted in the figure, in which the outlet opening 7 of the measurement gas sensor 5 communicates via valve 20 and membrane equilibrator 4 with the surrounding water 2. In the second possible switching state of valve 20 and outlet line 30, on the other hand, the outlet opening 7 of the measurement gas sensor 5 is connected to an input 21 of the reference gas source 17, in which the outlet opening 7 of the measurement gas sensor 5 in this switching state is not connected to the surrounding water 2 via the membrane equilibrator 4. In the second possible switching state of valve 20 in the outlet line 13 with corresponding position of valve 16 in the inlet line 8 a bypass line that connects the inlet opening 8 with the outlet opening 7 of the measurement gas sensor 5 is switched, in which case the bypass line in this switching state of valves 20, 16 connects the outlet opening 7 with the inlet opening 6 of the measurement gas sensor 5 via the valve 20 and the outlet line 13, the reference gas source 17, the valve 16 and the inlet line 8, pump 9 and heating device 10. In this switching state gas circulates through the measurement gas sensor 5 within housing 3 of the partial pressure sensor 1 without gas exchange occurring with the surrounding water 2 via membrane equilibrator 4.

Finally, the partial pressure sensor 1 according to FIG. 1 includes an only schematically depicted control and evaluation unit 22. The control and evaluation unit 22 is connected via a control line 23 to valve 16, 20 and outlet line 13 and in inlet line 8 in order to switch the valve 16, 20 between the described possible switching states. In addition, the control and evaluation unit 22 is connected via a signal line 24 to readout devices 25 for readout of the measurement gas sensor 5. Finally, the control and evaluation unit 22 is connected via additional signal lines not shown in the figure to sensors 18, 19, 11, 12, 14, 15 for temperature, moisture and pressure in order to determine the partial pressure by means of the absorption signal detected by the optical measurement gas sensor 5.

The control and evaluation unit 22 has means to store the measured values read out via the readout device 25 from the measurement gas sensor 5. In addition, means for analysis and processing of the measured data are provided in the control and evaluation unit.

Figure 2:
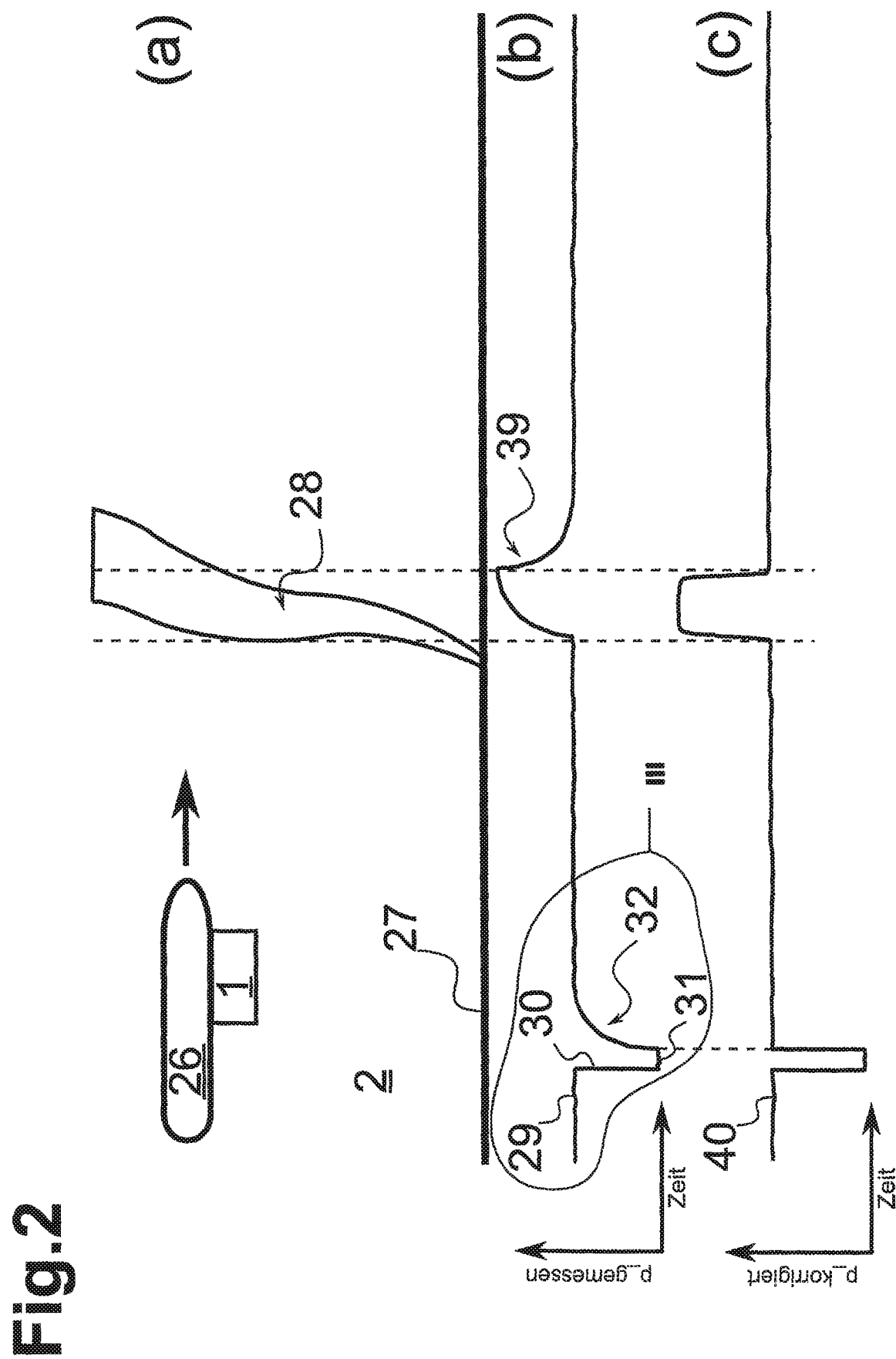
FIG. 2: schematic depiction to show the preferred embodiment of the method according to the invention for determination of response characteristics.

FIG. 2 schematically depicts a preferred variant of the method according to the invention for operation of a partial pressure sensor 1 according to FIG. 1. In part a) of FIG. 2 an instrument support 26 is shown, which can be an AUV (autonomous underwater vehicle), ROV (remotely operated vehicle) a ship or the like. The partial pressure sensor 1 according to FIG. 1 is fastened to the instrument support 26. As indicated by an arrow in FIG. 2A, the instrument support 26 with the partial pressure sensor 1 according to the invention fastened to it is moved over the sea bottom 27 through the surrounding water in the direction of the arrow. In the forward movement direction of instrument support 26 and area 28 with increased measurement gas concentration is schematically shown. For example, this is carbon dioxide, which emerges into the water tube from a source in sea bottom 27. The spatial position and extent as well as partial pressure of the area 28 with increased measurement gas concentration is now to be measured as precisely as possible with the partial pressure sensor 1 arranged on the instrument support 26, while the instrument support 26 is moved through area 28 with a specific speed.

In order to counteract the problems occurring during this measurement by the moving instrument support 26 in conjunction with a finite response time of the partial pressure sensor 1 to changes in the measured signal, i.e., changes in the partial pressure of the measurement gas, according to the invention determination of the response characteristic of the partial pressure sensor 1 is initially conducted as follows while the instrument support 26 with the partial pressure sensor 1 is moved in an area of sufficient distance from the area 28 with increased measurement gas concentration in which a constant partial pressure of the measurement gas prevails.

As shown in FIG. 1, a bypass line between outlet opening 7 and inlet opening 6 of the measurement gas sensor 5 is initially created via the control and evaluation unit 22 by switching valve 20 in the outlet line 13 and valve 16 in the inlet line 8, which is passed through the reference gas source 17. The surrounding gas passed through the reference gas source 17 is then converted to reference gas in the reference gas source. In the example considered here, in which the measurement gas is carbon dioxide, conversion occurs by passing the surrounding gas through a column of soda lime. In one variant of the invention, in which methane is the measurement gas, conversion can occur by oxidation with the oxygen contained in the surrounding gas in order to generate $CO_2$ and $H_2O$ on a thermocatalytic element, which can be present in the form of a thermocatalytic sensor as catalytic oxidation sensor.

The measurement gas sensor 5 according to the practical example is only sensitive to $CO_2$. After passing through reference gas source 17 reference gas, i.e., surrounding gas which contains no $CO_2$ therefore enters valve 16 in inlet line 8 and is introduced via pump 9 and heating device 10 through the inlet line 6 into the measurement space of the measurement gas sensor 5. A time series 29 of recorded measurement data read out from the measurement gas sensor 5 via the readout device 25 of the control and evaluation unit 22 is shown in FIG. 2B. The time series 29 is arranged in FIG. 2B beneath the three-dimensional sketch according to FIG. 2A so that it is apparent which measurement location, i.e., which position of the partial pressure sensor 1 fastened to the instrument support 26 corresponds to a measurement point of the time series 29.

In the time series 29 according to FIG. 2B it is now apparent that the described flow through the measurement space is the reference gas generated in the reference gas source 17 leads to an abrupt drop 30 in the measurement signal in time series 29. It is further apparent that the measurement signal during flow through the measurement space of the measurement gas sensor 5 assumes a reference plateau 31 with the reference gas. After the reference plateau 31 is reached, the time series 29 of the measurement signal corresponds to the actual partial pressure in the measurement space of measurement gas sensor 5, since the stationary state is reached at which any effects caused by a delayed response behavior no longer play a role. The reference plateau 31, as is known, can also be used for calibration of the measurement gas sensor 5 in order to correct for any reference point shift of the measurement gas sensor.

The flank-like rise 32 of the measurement signal connected to the reference plateau 31 is also apparent in the time series 29 of the recorded measured data according to FIG. 2B, which is recorded when the valve 16 in the inlet line 8 and the valve 20 in the outline line 13 are switched so that the reference gas source 17 is no longer connected to the measurement space of the measurement gas sensor 5 and flow through the measurement gas sensor 5 instead occurs with surrounding gas drawn into inlet line 8 via the membrane equilibrator 4.

Since, as comparison with FIG. 2A shows, in which the spatial segment of the partial pressure of the measurement gas, for example, carbon dioxide, corresponding to the flank-like rise 52 of the time series 29, does not change, an abrupt rise at the reference plateau 31 should be connected instead of the flank-like rise 32 during an ideal measurement. The fact that the flank-like rise 32 is recorded instead is attributed to the response characteristic of the partial pressure sensor 1, which is influenced by the all the components of the partial pressure sensor 1. This includes the membrane equilibrator 4, the valve 16 and inlet line 8, the pump 9, the heating device 10, the measurement gas sensor 5, the valve 20 and outlet line 13. Since the real measured quantity rises abruptly during flow of reference gas through the measurement gas sensor 5 in situ according to the invention with essentially constant partial pressure of the measurement gas, for example, carbon dioxide, the response characteristic of the measurement gas sensor 5 can be determined by evaluating the flank-like rise 32.

Figure 3:
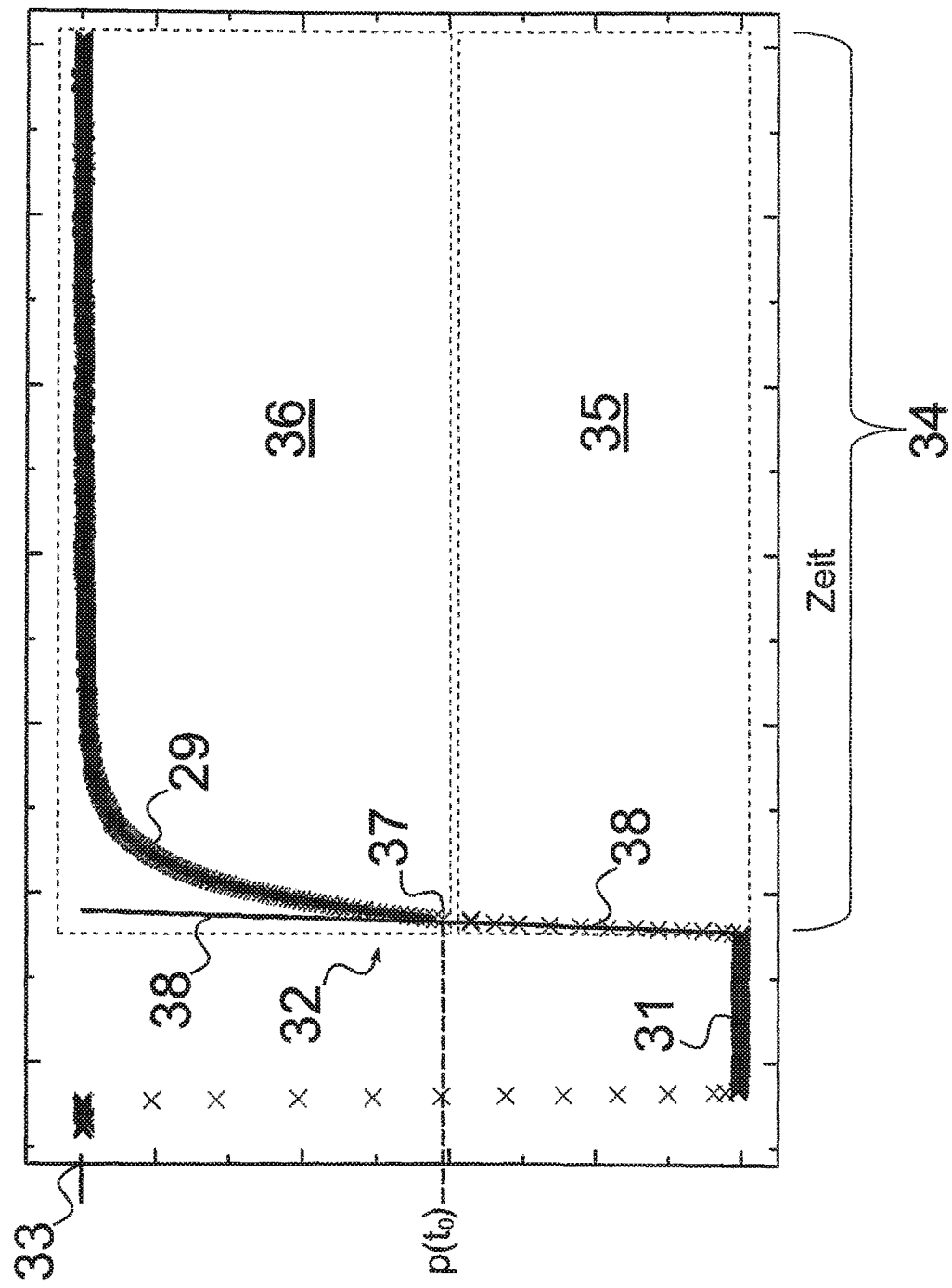
FIG. 3: example of a measurement series which was determined during performance of the method for determination of the response characteristic in order to show a preferred embodiment of the method for determination of the response characteristics.

Determination of the response characteristic by evaluation of the flank-like rise 32 is further explained in FIG. 3. FIG. 3 shows an enlargement of area 3 of the time series 29 according to FIG. 2B in order to show the method according to the invention for determination of the response characteristic of the measurement gas sensor 5. As is apparent in FIG. 3, the measurement series initially shows the initial partial pressure 33 of the measurement gas in water 2, which prevails at the position of the instrument support 26 and therefore the partial pressure sensor 1 depicted in FIG. 2A. The measured and actual partial pressures disappear roughly in the area of reference plateau 31.

To evaluate the response characteristic by means of the flank-like rise 32 of the time series 29 the procedure according to the invention is as follows according to the practical example described here. The evaluation of the flank-like rise 32 is based on an evaluation series within a calibration interval 34, during which the partial pressure of the measurement gas in the surroundings is constant, as is apparent in FIG. 2A. Initially the area of the flank-like rise 32 was divided analytically into a first section 35, which was recorded during a mixing phase of the measurement gas with the reference gas in the measurement space of the measurement gas sensor 5, and a second section 36. Values directly connected to the reference plateau 31 up to a transition point 37 then correspond to the first section 35 of the measurement series 29. The second section 36 of the measurement series 29 accordingly extends over measurement points from the transition point 37 to the last measurement point within the calibration time interval 34.

To determine the transition point 37 a regression line 38 is determined according to the invention starting from the first measured values in the measurement series 29 which are connected to the reference plateau 31. The transition point 37 is then obtained by determining the point at which the measured values leave the regression line 38. Analytically this is the point at which the residuum between the actual measured values and the corresponding values on the regression 38 exceeds the specific value.

In the next step with consideration of only the second section 36 of the measurement series 29 a regression analysis is performed in which the measurement values within the second section of the measurement series 36 are adjusted to the following model:

$$p_{(t)} = p_{water} + (p_{(t_0)} - p_{water})e^{-\frac{t}{\tau}}$$

in which $p_{(t)}$ corresponds to measured values of the time series 29 in the second section 36, $p_{water}$ corresponds to the initial partial pressure 33 of the measurement gas and $p_{(t_0)}$ corresponds to the output signal of the measured partial pressure at time $t_0$, i.e., at transition point 37 and in which $\tau$ denotes a time constant to be determined in the context of a regression analysis.

With the described method the response characteristics of a partial pressure sensor 1 is determined according to the invention in situ. The regression parameters, especially parameter $\tau$, implicitly allow for with great advantage all factors that influence the response characteristic of the partial pressure sensor 1 at the location of the measurement, like temperature, pressure, properties of the membrane equilibrator 4, etc.

With reference to FIG. 2A the subsequent measurement process is then shown. The instrument support 26 is moved after the response characteristic has been determined with the described method through the area 28 with increased measurement gas concentration. A raw measurement response 39 is then recorded in the time series 29 of the recorded measurement data. This is necessarily distorted by the response characteristic of the partial pressure sensor 1. Based on the determination of the response characteristic described with reference to FIG. 3 in detail, the method according to the invention now permits computer compensation of the measured data of the time series 29. This occurs according to the practical example described here by means of the formula:

$$p_{water} = \frac{p(t) - p(t_0)e^{-\frac{t}{\tau}}}{1 - e^{-\frac{t}{\tau}}}$$

In a typically discretely recorded measurement series 29 evaluation of this formula in practice occurs through the following iterative formula:

$$p_{corrected, t_{i+1}} = \frac{p(t_{i+1}) - p(t_i)e^{-\frac{\Delta t}{\tau}}}{1 - e^{-\frac{\Delta t}{\tau}}} \text{ with } \Delta t = t_{i+1} - t_i$$

The times $t_{i+1}$ and $t_i$ then denote values of the time series 29 occurring in succession, in which it must be kept in mind that $\Delta t$, i.e., the scanning rate, is chosen small enough that the partial pressure of the measurement gas in water 2 can be assumed constant within this time interval. This is therefore evaluated according to the partial pressure gradient in water 2.

If one now applies the mentioned correction to the time series 29 of the measurement data recorded via the readout device 25 of the measurement gas sensor 5, the corrected measurement series 40 depicted in FIG. 2C is obtained, which reflects a correct chronological and therefore spatial assignment of the measured values to the measurement conditions explained in FIG. 2A with respect to partial pressure of the measurement gas. In particular, it is apparent that a rectangular jump function is shown in the initial area, which corresponds to the above described zeroing process. It is also apparent how a spatially correct assignment of the measured data to the area 29 with increased measurement gas concentration occurs, especially the raw measurement response 39.

One skilled in the art will recognize that the data analysis, especially the regression analysis requires appropriate generally common data filtering.

By means of the figures a device according to the invention as well as a method according to the invention for its operation are therefore described, which permits by means of in situ zeroing, i.e., in situ determination of the response behavior of the partial pressure sensor 1, improved measurement of the measurement gas in the surrounding gas. The improvement pertains in particular to an improved spatial and chronological assignment of the measured values to the real partial pressure conditions.

The described flow through the measurement gas sensor 5 by corresponding switching of valve 16, 20 and subsequent determination of the response behavior can be conducted repeated in situ according to the invention, especially after surrounding parameters have changed. A conversion of the time series 29 by means of the response characteristic to the actual values 40 according to FIG. 2C then occurs based on the last determined response characteristic.

Between such determinations of the response characteristic a computer correction of the response characteristic can also be conducted in the context of the invention by means of the values for temperature, moisture and pressure measured in the surrounding water 2, i.e., outside the partial pressure sensor 1, if a corresponding model on the dependence of the response characteristic on these parameters is used as a basis.

The method described with reference to FIGS. 2 and 3 is implicitly based on the fact that the surrounding gas at the location and performance of the zeroing method according to the invention contains measurement gas with a non-negligible initial partial pressure 33. Since the partial pressure sensor 1 is a partial pressure sensor provided with a measurement gas sensor 5 for $CO_2$, which is designed for detection of $CO_2$ in the surrounding gas, this condition is generally the case during use of the partial pressure sensor 1 in water 2 described in the figures. A surrounding air dissolved in water normally has a partial pressure for $CO_2$ lying above the detection limit of the measurement gas sensor 5.

Figure 4:
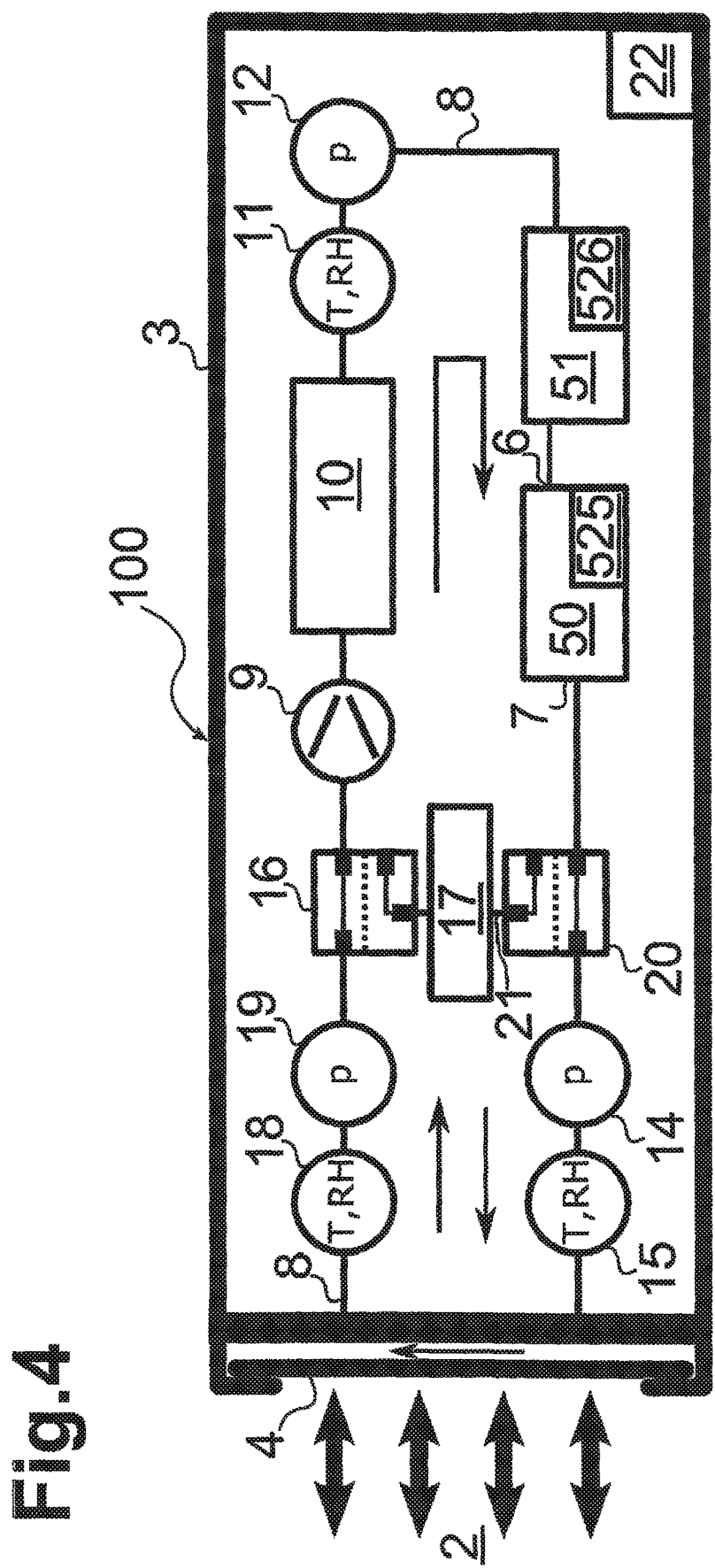
FIG. 4: schematic depiction of another preferred variant for underwater use of a detection device according to the invention.

If, on the other hand, the zeroing method according to the invention is to be conducted at a location at which the measurement gas has an unduly low initial partial pressure 33 within the surrounding gas, which is smaller than the detection limit than the measurement gas sensor 5, the evaluation method described with reference to FIG. 3 cannot be conducted or not conducted with satisfactory results for the response characteristic. In such cases a method according to a modification of the invention with the schematically depicted partial pressure sensor 100 can be carried out in the context of the invention. The partial pressure sensor 100 according to FIG. 4 is designed to detect the partial pressure of methane gas as measurement gas in the surrounding gas. Methane gas, on the other hand, in many cases is normally not present above a detection limit in the surrounding gas.

The partial pressure sensor 100 is designed essentially similar to the partial pressure sensor 1 according to FIG. 1. However, instead of measurement gas sensor 5 for $CO_2$, which is used in the partial pressure sensor according to FIG. 1, the measurement gas sensor 50 is arranged, which is sensitive to methane gases as measurement gas in the surrounding gas. A correction gas sensor 51 is connected in series upstream of the measurement gas sensor 50 sensitive to methane gas in the inlet line 8. The correction gas sensor 51 is in principle a sensor similar to the measurement gas sensors 5, 50. However, the correction gas sensor 51 is sensitive to $CO_2$ gas as measurement gas in the surrounding gas.

If the zeroing method is now carried out by appropriate switching of valve 16, 20 for flow of the reference gas source 17, this means, as described at length above, that the inlet line 8 and therefore the correction gas sensor 51 and the measurement gas sensor 50 for $CH_4$ is traversed with a gas from which the $CO_2$ fraction was removed by passing through reference gas source 17 and which also contains no methane gas ($CH_4$) from the outset. For the measurement signal of the measuring gas sensor 50, which reacts exclusively to methane gas as measurement gas, this does not lead to a change. Before, during and after zeroing the gas fed to the measurement gas sensor 50 contains no methane gas. The measurement signal which is recorded by the correction gas sensor 51 exhibits the behavior explained at length with reference to FIG. 3, which permits determination of the response behavior. Based on a calibration performed under laboratory conditions, the correction response characteristic of the reference gas sensor 50 determined in the described manner then permits a conclusion concerning the sought response characteristic of the partial pressure sensor 100.

Although two series-connected gas sensors 50, 51 are schematically depicted in FIG. 4, one gas sensor can likewise be used, in which, in addition to the detector for the measurement gas, in this example methane, an additional detector for the reference gas, here $CO_2$-free gas, can be used, which measures the partial pressure of the reference gas within the same measurement chamber.

LIST OF REFERENCE NUMBERS

1 Partial pressure sensor
2 Water
3 Housing
4 Membrane equilibrator
5 Measurement gas sensor for CO2
6 Inlet opening
7 Outlet opening
8 Inlet line
9 Pump
10 Heating device
11 Sensor for temperature and moisture
12 Pressure sensor
13 Outlet line
14 Pressure sensor
15 Sensor for temperature and moisture
16 Valve
17 Reference gas source
18 Sensor for temperature and moisture
19 Pressure sensor
20 Valve
21 Input
22 Control and evaluation unit
23 Control line
24 Signal line
25 Readout device
26 Instrument support
27 Sea bottom
28 Area with increased measurement gas concentration
29 Time series of measurement data recorded via the readout device
30 Abrupt drop
31 Reference plateau
32 Flank-like rise
33 Initial partial pressure
34 Calibration time interval
35 First section of the measurement series
36 Second section of the measurement series
37 Transition point
38 Linear regression line
39 Raw measurement response
40 Corrected measurement series
50 Measurement gas sensor for CH4
51 Correction gas sensor for CO2
100 Partial pressure sensor for CH4
525 Readout device
526 Readout device

What is claimed is:

1. A method of operation of a measurement space and a measurement gas sensor sensitive to a measurement gas contained in a surrounding gas for measurement of a quantity that characterizes the partial pressure of the measurement gas in the measurement space, comprising:
   detecting a partial pressure of the measurement gas, and determining the response characteristic of a device including
   a. traversing the measurement space with a reference gas, wherein the measurement gas sensor and/or a correction gas sensor sensitive to a correction gas is not sensitive to said reference gas, observing an output signal of the measurement gas sensor and/or an output signal of the correction gas sensor until it reaches an essentially constant minimal value;
   b. traversing the measurement space with a surrounding gas after the output signal has reached the essentially constant minimal value, and recording the output signal of the measurement gas sensor and/or the output signal of the correction gas sensor in a measurement series with time resolution during a calibration time interval; and
   c. evaluating the measurement series to determine the response characteristic.

2. The method of claim 1, evaluating the measurement series initially a correction response characteristic is determined based on the output signal of the correction gas sensor and the response characteristic of the device is determined from the correction response characteristic.

3. The method of claim 1, wherein the output signal of the measurement gas sensor is corrected by the response characteristic in order to obtain a chronological assignment of the output signal through the partial pressure of the measurement gas at the time of recording of the output signal.

4. The method of claim 1, wherein the calibration time interval is chosen so that the partial pressure of the measurement gas and/or the partial pressure of the correction gas is essentially constant during the calibration time interval.

5. The method of claim 1, wherein the determining of the response characteristic a first section of the measurement series which was recorded during a mixing phase with the surrounding gas with the reference gas in the measurement space is not considered.

6. The method of claim 5, wherein the first section of the measurement series extends to a transition point from an essentially linear to an essentially exponential curve trend.

7. The method of claim 1, wherein the response characteristic is determined by a regression analysis of the measurement series, using the following model:

$$p_{(t)} = p_{water} + (p_{(t_0)} - p_{water})e^{-\frac{t}{\tau}}$$

in which P(t) denotes the output signal at time t, $p_{water}$ denotes the partial pressure of the measurement gas within the surrounding gas, $p(t_o)$ denotes the output signal at time $t_o$ and $\tau$ denotes a time constant.

8. The method of claim 1, wherein the output signal of the measurement gas sensor is corrected by means of the response characteristic in which the output signal p(t) at time t is assigned to the partial pressure $p_{water}$ of the measurement gas within the surrounding gas at the time of recording of the output signal according to the following formula:

$$p_{water} = \frac{p(t) - p(t_0)e^{-\frac{t}{\tau}}}{1 - e^{-\frac{t}{\tau}}}$$

in which $p(t_o)$ is the output signal at time $t_o$.

9. The method of claim 1, wherein determining a response characteristic is conducted several times, especially after each significant change of one or more surrounding parameters.

* * * * *